(12) United States Patent
Cueto-Garcia

(10) Patent No.: US 8,252,333 B2
(45) Date of Patent: Aug. 28, 2012

(54) BIODEGRADABLE, NON-TOXIC BIOLOGICAL ADHESIVE FOR USE IN ABDOMINAL SURGERY

(76) Inventor: Jorge Cueto-Garcia, Bosques Lomas (MX)

( * ) Notice: Subject to any disclaimer, the term of this patent is extended or adjusted under 35 U.S.C. 154(b) by 802 days.

(21) Appl. No.: 11/507,623

(22) Filed: Aug. 22, 2006

(65) Prior Publication Data
US 2007/0202173 A1    Aug. 30, 2007

Related U.S. Application Data

(60) Provisional application No. 60/762,136, filed on Jan. 26, 2006.

(51) Int. Cl.
*A61K 9/10* (2006.01)
*A61K 31/718* (2006.01)
*A61K 31/715* (2006.01)
*A61K 31/70* (2006.01)
*A61K 33/30* (2006.01)

(52) U.S. Cl. ........ 424/488; 424/484; 424/425; 424/426; 424/78.06; 424/641; 424/642; 514/58; 514/60

(58) Field of Classification Search ........... None
See application file for complete search history.

(56) References Cited

U.S. PATENT DOCUMENTS

| | | | |
|---|---|---|---|
| 3,667,472 A | 6/1972 | Halpern | |
| 4,600,574 A | 7/1986 | Lindner et al. | |
| 4,889,844 A * | 12/1989 | Silvetti et al. | 424/78.25 |
| 4,990,339 A * | 2/1991 | Scholl et al. | 424/443 |
| 5,004,767 A * | 4/1991 | Krause et al. | 524/30 |
| 5,496,872 A | 3/1996 | Constancis et al. | |
| 5,587,175 A | 12/1996 | Viegas et al. | |
| 5,932,639 A * | 8/1999 | Eden et al. | 524/48 |
| 5,955,096 A | 9/1999 | Santos et al. | |
| 5,985,312 A | 11/1999 | Jacob et al. | |
| 6,046,178 A | 4/2000 | Silvetti, Sr. | |
| 6,123,965 A | 9/2000 | Jacob et al. | |
| 6,156,348 A | 12/2000 | Santos et al. | |
| 6,368,586 B1 | 4/2002 | Jacob et al. | |
| 6,582,720 B1 | 6/2003 | Inagi et al. | |
| 6,770,148 B1 | 8/2004 | Naggi et al. | |
| 2001/0000142 A1 | 4/2001 | Santos et al. | |
| 2003/0077317 A1 | 4/2003 | Santos et al. | |
| 2004/0116511 A1 * | 6/2004 | Malik | 514/453 |
| 2004/0208906 A1 | 10/2004 | Tatara et al. | |
| 2005/0113937 A1 | 5/2005 | Binette et al. | |

FOREIGN PATENT DOCUMENTS

| | | |
|---|---|---|
| EP | 0 815 879 | 1/1998 |
| EP | 1 085 920 | 3/2001 |
| EP | 1 248 636 | 10/2002 |
| WO | WO 97/00868 | 1/1997 |
| WO | WO 99/58168 | 11/1999 |
| WO | WO 03/068200 | 8/2003 |

OTHER PUBLICATIONS

Wetter, L., et al. Scand. J. Plast. Reconstr. Surg. (1986) 20; 165-172.*
Communication dated Mar. 3, 2010 issued by the European Patent Office in related European Application No. 07 808 494.4 (4 pages).

* cited by examiner

*Primary Examiner* — Kevin S Orwig
(74) *Attorney, Agent, or Firm* — Robert P. Michal; Lucas & Mercanti, LLP

(57) ABSTRACT

A biological adhesive formulation comprising dextrin, at least one adhesiveness modifier agent, and at least one antibiotic is suitable for promoting healing of tissue in a patient, for example, to prevent anastomosis of a surgical wound in the digestive system of a patient, and for affixing a prosthesis during a hernia operation.

24 Claims, 4 Drawing Sheets

BIODEGRADABLE, NON-TOXIC BIOLOGICAL ADHESIVE FOR USE IN ABDOMINAL SURGERY

This application claims the benefit of U.S. Provisional Application Ser. No. 60/762,136, filed Jan. 26, 2006, the entire disclosure of which is hereby incorporated by reference.

FIELD OF THE INVENTION

The invention relates to a biological adhesive for surgical use in humans. In particular, this invention relates to a biologically adhesive formulation that is biodegradable, non-toxic, offers temporary protection of anastomosis within, for example, the gastrointestinal tract, and reduces or eliminates to the maximum dehiscences and their serious consequences. Additionally, the present invention relates to a temporary adhesive to affix a prosthesis during inguinal hernioplasties and an adhesive for occluding fistulas.

BACKGROUND OF THE INVENTION

The capacity to unite biological tissues and/or to protect these unions (i.e., "anastomosis") has been an area of very important research for the biomedical investigators for several decades.

One of the greater problems that plague patients and surgeons world-wide is proper healing of an anastomosis within the gastrointestinal system and those of other systems as well. Dehiscence or faulty healing of the anastomosis may occur even though the anastomosis is well indicated, in the appropriate patient, and is adequately performed. Some dehiscences carry a high mortality rate (30-50%) and their complications require urgent reoperations and prolonged hospitalization in the intensive therapy units involving, for example, parenteral nutrition, complicated respiratory care, prolonged and costly antibiotic-therapy, numerous laboratory tests, etc.

At the present time, obesity has reached epidemic proportions throughout in the world, in developed as well as in underdeveloped countries. For example, in the United States of America one of every three adults is obese and approximately 5% suffer from morbid obesity, i.e., a body mass index (BMI) of 35 kg/m$^2$ or greater, and, what is worse, 1 of each 6 children suffers from obesity[1,2]. Although numerous medical treatments exist, these treatments only aid those patients with lower degrees of obesity, or in the short term, patients with morbid obesity, since, although initially the patients loose weight, a follow-up 10 to 15 years after the treatment demonstrates that 98% of the patients have returned to their initial levels of obesity ("bounce"). Thus, they remain obese and frustrated.[1-4] Morbid obesity is recognized at the present time as a chronic, incurable multi-factorial disease, the effects of which damage several organ systems that not only decrease the duration of life, but also the quality of life as well. Obesity affects the organism through the so-called co-morbidities, the most important ones being diabetes mellitus II, arterial hypertension, ischemic accidents of the heart and the cerebral circulation, serious pulmonary complications such as sleep-apnea, pulmonary disease of the obese, thromboembolic accidents, gastroesophageal reflux, several osteo-articular disorders, alterations of fertility, urinary incontinence, dislipidemias, etc[1-6]. Moreover, objective evidence exists that obesity is a predisponent factor for the development of several malignant tumors such as breast cancer, colon-rectal cancer, prostate cancer, endometrial cancer, myelomas, leukemias, etc.[1-4]

Since the world-wide consensus meeting of 1991 in the United States of America, at the National Institutes of Health (NIH), [4]it has been concluded that surgery is the only effective method for the control of the complications of obesity. With the introduction of the laparoscopic surgery everywhere in the world, the number of procedures of Bariatric surgery has increased in exponential form. But, due to economic reasons in some regions of the world, it is still practiced in conventional or open technique, which is also appropriate.[1-6]

The two main causes of mortality, major complications and enormous costs of gastric bypass, bilio-pancreatic diversions, etc., are the improper healing of the anastomosis called dehiscence (a premature bursting open or splitting along a surgical suture line, like in the junction or connection between the ends of the intestine, or the stomach pouch and the intestine as in the gastric bypass) and pulmonary thromboembolism[5-8]. The prevalence of the first varies from 1 to 5% in general, it being less in some groups with more experience[5-13]. The mortality caused by the anastomotic dehiscence ranges from 30 to 50%. Serious peritonitis ensues in patients that are already complicated with pulmonary, circulatory problems, etc., and require immediate and urgent reoperations, as well as special treatment in an intensive care unit, as mentioned before, which is extremely expensive. The cost for the patients who survive is approximately $ 100,000 USD[12]. If 200,000 annual procedures are practiced in the USA, and if the prevalence of leaks is 2% (that at general level is greater), this would mean that the cost of these complications would be more than 20 million dollars annually, without taking into account indirect costs of the family, medico-legal and others.

This feared anastomotic dehiscence also occurs in surgery of the colon and rectum. The complications of diverticular disease are more and more frequent in patients older than 50 years (considering that life expectancy continues to increase everywhere in the world), like ischemic accidents, malignant tumors, volvulus, etc. The prevalence of dehiscences in anastomosis of the colon and rectum is greater than in Bariatric surgery and ranges from 5 to 15% of the cases reported in general. Also, mortality in these patients is greater, and the expenses in the intensive care unit are also very high for obvious reasons[14-21]. Colonic dehiscences, in addition, diminish survival rates for patients operated on for cancer[22]. When these patients are operated in elective or emergency situations, it is necessary to extirpate a segment of intestine. In debilitated, older patients, frequently with peritonitis, it is not possible to practice a primary anastomosis, but instead it is necessary to perform a colostomy or ileostomy. Colostomies save many lives but nobody likes them. They require special care in all patients, and almost all patients want to be re-operated on so that the intestine can be re-connected and they can live normally. But, that also means another surgery, additional risks, expenses, etc.

Because endoscopic surgery is already accepted internationally as adequate for colon cancer treatment[16,21], as for well as non-malignant diseases[17-20], the number of these procedures performed will increase, as happened with cholecystectomy, antireflux surgery, nephrectomy for renal donor and many other procedures.

In the esophagus, the situation is more serious than in the colon, since the organ does not have a serous layer and anastomotic leaks (for example, in resections for tumors, congenital diseases, caustic burns, antireflux reoperations, etc.) produce mediastinitis with very high mortality rates.[23-25]

It was mentioned previously that anastomosis can present dehiscences in spite of being well indicated, well done manually, with staples or using a mixed technique, without tension, with good blood supply, with good nutritional status, without peritonitis, regardless of being elective or urgent. It is very important to mention that dehiscences appear between the second and tenth postoperative day, but 98% occur between the second and sixth post operative day.[26,27]

During the $2^{nd}$ thru the $8^{th}$ postoperative day, the anastomosis does not have any strength by itself. In this time period, collagen deposition and new tissue bridges have not yet been built across the two ends ($2^{nd}$ phase of healing process). As a result, the anastomosis is very weak, inflamed due to the presence of sutures and staples (foreign bodies) and bacteria, clots, etc. It is precisely during this time period that anastomosis leaks (or failures) often occur with the ensuing very grave and often lethal complications.

Anastomotic dehiscences, like a perforated duodenal ulcer, initially produce a discharge of gastrointestinal secretions that cause an intense, localized inflammatory reaction called "chemical peritonitis." Later on, the discharge process continues and more secretions and bacteria are discharged producing secondary peritonitis, a most feared cause of mortality.[27-29]

In the case of peritonitis by perforation and/or dehiscence of the colon, the peritonitis is of fecal type from the beginning and therefore of greater gravity in patients that, e.g., due to their age, other cardio-pulmonary ailments, metabolic complications, malnourishment, etc., have a greater surgical risk from the outset.[17-20]

In the esophagus, something similar happens with the discharge of diverse pathogenic germs in the mediastinum. Some groups such as Schardey et al. of Germany, affirm, based on their experimental and clinical observations, that " . . . it can be prevented that the potentially pathogenic germs associated with the micro-leaks are in contact . . . and produce these dehiscences." by means of the use of intensive antibiotic therapy.[23,24]

A person knowledgeable in the area knows that in mammals in the healing process there are 3 main phases. The first phase starts immediately following the traumatic event with clotting accompanied by acute inflammation and, only after 7-8 days, the collagen deposition or second phase begins. The resultant scar is remodeled in the 3rd phase and then, there is considerable strength in this area weeks later. In the intestinal anastomotic area there is acute inflammation, clots, bacteria and secretions and it is known that during these days there is no collagen deposition in the edges. For this reason, the segments of intestine are held only by the sutures and/or staples, without bridges of new tissue to join both ends, but the anastomosis itself does not have any intrinsic firmness or strength per se. It is precisely in this critical period that most anastomotic failures or dehiscences occur. (Wasserberg N, Tzakis A G, Santiago S F, Ruiz Ph, Salgar Sh K., Anastomotic healing in small bowel transplantation model in the rat, World J Surg 2004; 28:69-73.). The method and adhesive herein described provide protection of the anastomosis during these critical days to prevent a dehiscence or failure to heal adequately.

In the case of fistulas that can be a consequence of an anastomotic dehiscence or trans-operative trauma, etc., they represent a very serious and annoying complication of various surgical procedures and some diseases of diverse organ systems like the gastrointestinal, respiratory, urinary, etc. When fistulas are not accompanied by obstruction or complicated with active suppuration, one can try to obliterate them with different methods or sealants with variable results[30-33].

In inguinal, incisional and other parietals hernias, the "gold standard" surgical treatment nowadays is called "without-tension" wherein a prosthesis or mesh is placed in the defect.[34-37]. Fixation of this prosthesis can be performed in several ways to avoid its displacement, both in open or laparoscopic surgery, frequently using sutures or staples. Staples are very expensive and, like sutures, they can incorporate, catch or compress small nerves, or produce osteo-condritis and post operative pain. Post operative neuritis is one of the frequent and important complications in inguinal hernia operations and, unfortunately, a frequent cause of reoperations and legal actions. The effect of fixation in this case is also temporary since after 4 to 5 days the prosthesis is included by the local connective tissue and no longer will be displaced[37]. A brief inspection in the surgical congresses and current literature shows that great interest exists to find an effective and safe method of affixing prosthesis in these situations. In fact, novel methods and alternatives are continuously described.[38,39]

U.S. Pat. No. 6,046,178 discloses a "wound treating" composition comprising a starch hydrosylate, such as maltodextrin, for treating open wounds or gaps in the skin tissue as in the treatment of burns, ulcers, lesions, and other skin defects. The starch hydroxylate is combined with sterile water and a gelatinization agent such as glycerin to form an emulsion. The starch hydroxylate mixes with the proteins in the wound fluid and forms a film that ultimately adheres to underlying tissue. The formed film is semi-permeable to air and fluid. U.S. Pat. No. 6,046,178 does not teach or suggest an adhesive or glue to be used in surgical practice for temporarily reinforcing and protecting the anastomosis of the digestive system (and of other organ systems), nor occluding fistulas nor affixing prosthesis in inguinal hernioplasties.

U.S. Pat. No. 5,985,312 describes using metal compounds such as zinc oxide to enhance the bioadhesiveness of polymers used in drug delivery devices such as microspheres, tablets, capsules, which contain a drug or a diagnostic agent. U.S. Pat. No. 5,985,312 does not suggest a bioadhesive polymer such as polysaccharide for use in surgical practice for temporarily reinforcing and protecting the anastomosis of the digestive system (and of other organ systems).

U.S. Pat. No. 4,600,574 disclose a tissue adhesive in which a tissue-compatible material such as polysaccharide is combined with a solution comprising fibrinogen and Factor XIII. Due to the presence of fibrin, this adhesive suffers from the disadvantages as discussed further below.

U.S. Pat. No. 5,496,872 disclose a non-toxic, biodegradable adhesive composition for surgical use. The composition contains a compound having at least two relative functions which can be used in combination with a biodegradable, synthetic or natural polypeptides such as polysaccharides.

SUMMARY OF THE INVENTION

Thus, in accordance with the invention, there is provided a technique involving a tissue adhesive or glue that protects and/or promotes the normal healing of tissues. This technique solves at least some of the problems associated with leaking of anastomosis and affixing prosthesis in inguinal and other hernia operations. Additionally, there is provided a composition for use in the above mentioned technique.

According to a further aspect of the invention, there is provided a biological adhesive formulation comprising dextrin as a dispersion, at least one adhesiveness modifier agent, and at least one antibiotic, wherein the formulation contains 80-97 weight % of the dextrin dispersion, and the dextrin dispersion contains 45-75% solids, based on the total weight of the formulation. According to a further aspect of the invention, there is provided a biological adhesive formulation consisting essentially of dextrin as a dispersion, at least one adhesiveness modifier agent, and at least one antibiotic, wherein the formulation contains 80-97 weight % of the dextrin dispersion, and the dextrin dispersion contains 45-75% solids, based on the total weight of the formulation.

According to a further aspect of the invention, there is provided a biological adhesive formulation comprising dextrin as a dispersion, at least one adhesiveness modifier agent, and at least one antibiotic, wherein the formulation contains 80-97 weight % of the dextrin dispersion, the dextrin dispersion contains 45-75% solids, based on the total weight of the formulation, and the formulation has a viscosity of 12,000-25,000 cp, preferably 15,000-18,000 cp.

According to another aspect of the invention, there is provided a method for promoting healing of tissue in a patient comprising applying to the tissue an adhesive formulation comprising dextrin, at least one adhesiveness modifier agent, and at least one antibiotic. Preferably, the adhesive formulation comprises dextrin as a dispersion, at least one adhesiveness modifier agent, and at least one antibiotic, wherein the formulation contains 80-97 weight % of the dextrin dispersion, and the dextrin dispersion contains 45-75% solids, based on the total weight of the formulation.

According to another aspect of the invention, there is provided a method for preventing dehiscence of an anastomosis in a patient, comprising applying an adhesive formulation comprising dextrin, at least one adhesiveness modifier agent, and at least one antibiotic. Preferably, the adhesive formulation comprises dextrin as a dispersion, at least one adhesiveness modifier agent, and at least one antibiotic, wherein the formulation contains 80-97 weight % of the dextrin dispersion, and the dextrin dispersion contains 45-75% solids, based on the total weight of the formulation. According to a preferred embodiment, the wound is within the digestive system and the adhesive formulation protects against dehiscences of anastomosis of the digestive system.

According to another aspect of the invention, there is provided a method for affixing a prosthesis during a hernia operation in a patient, comprising applying an adhesive formulation comprising dextrin, at least one adhesiveness modifier agent, and at least one antibiotic. Preferably, the adhesive formulation comprises dextrin as a dispersion, at least one adhesiveness modifier agent, and at least one antibiotic, wherein the formulation contains 80-97 weight % of the dextrin dispersion, and the dextrin dispersion contains 45-75% solids, based on the total weight of the formulation. According to a preferred embodiment, the hernia operation is for an inguinal hernia.

According to another aspect of the invention, there is provided a method for occluding a fistula within a patient comprising applying to the fistula an adhesive formulation comprising dextrin, at least one adhesiveness modifier agent, and at least one antibiotic. Preferably, the adhesive formulation comprises dextrin as a dispersion, at least one adhesiveness modifier agent, and at least one antibiotic, wherein the formulation contains 80-97 weight % of the dextrin dispersion, and the dextrin dispersion contains 45-75% solids, based on the total weight of the formulation.

Multiple efforts have been made to develop synthetic polymers, such as, for example, the cyanoacrylates, as adhesives and sealants. The tissue adhesive disclosed in U.S. Pat. No. 3,667,472 (Halpern) relates to the surgical use of monomeric adhesives of $C_2$-$C_4$ alpha-cyanoacrylate. This tissue adhesive cures on contact with water or blood to form a solid layer which crystallizes over the tissue. Nevertheless, a disadvantage of this class of adhesives is that it is contraindicated for application in internal organs or vascular surgery, and therefore in anastomosis, due to its toxicity and oncogenic effects which have been well documented[30-31].

The well-known toxicity associated with synthetic adhesives has led investigators to develop biologically derived adhesives for use as union materials. One type of biological adhesive or glue is obtained from fibrin. Commercially, tissue adhesives of fibrin are derived from human plasma and thus raise potential risks to human health. Fibrin (and its derivatives) has been used in formulating biomedical adhesives with variable results from the experimental point of view and prospective studies in humans cannot be done for logical reasons. Its use for the protection of anastomosis has had apparently favorable results in a few reports. It is the only adhesive of use that is more or less accepted, but it is neither popular nor routine[31,32, 41-43]. Nevertheless, fibrin has several disadvantages: risk of viral transmission like any other cryoprecipitate exists; use of fibrin requires processes for extraction of blood; costs associated with fibrin are high; it requires a special applicator; risk of allergic reactions is always present; and a fatality has been reported. Another disadvantage with fibrin is that the adhesion force is relatively weak compared to other adhesives.

More recently, combinations of products have been devised to be used as adhesives and tissue sealants. One such combination that has been described is the use of a combination of three substances prepared separately, i.e., the cryoprecipitate of human fibrinogen, thrombin in the presence of the calcium ion, and concentrated factor XIII, used to obtain a glue biomedical applications. Nevertheless, this type of product and systems of adhesives available do not avoid the health problems described before. Attempts have been made to isolate an analogous component that contains fibrinogen (to see, for example, Feldman, M. C., ET al., Arch Otolaryngol-Head and Neck Surg (1988) 114:182-185; Feldman, M. C., ET al., Arch Ophthalmologic (1987) 105:963-967; Feldman, M. C., ET al., M J Otology (1988) 9:302-305; Silberstein L. E., ET to, Transfusion (1988) 28:319-321). However, the use of preparations of the analogous fibrinogen also has obvious limitations.

In summary, there is an acute need of a useful biomedical adhesive or sealant formulation that can be used in daily surgical practice to provide a fast and safe way to temporarily reinforce and protect the anastomosis of the digestive system and of other organ systems. Particularly, there exists need of a biological adhesive that allows effective temporary protection of the anastomosis between the second and sixth postoperative day, which is not toxic, does not produce serious adverse reactions, and minimizes demands on surgical resources and time, coupled with a superior biocompatibility and biostability. Additionally, such compositions preferably offer improved resistance to leakage where applied, without affecting the original physiological functions of the digestive system and other organ systems. Optimally, this formulation is inexpensive, in these present times of "cost containment".

These properties of the biological safe adhesive make it also useful for affixing prosthesis in different types of hernia operations.

Considering these needs, an aspect of the present invention is to provide an adhesive formulation based on a dextrin, which is safe and effective, and which has the following characteristics and properties:

i) Non-toxic. The dextrins are not toxic to human beings.

ii) Minimizes micro-leaks of liquids. Because dextrins have special properties to seal porous structures, their use in an adhesive provides an improvement over the other well-known agents.

iii) Adherent. Due to their adhesive properties, formulations of the present invention bind tissues through mechanical, chemical and/or electrostatic connections or unions among them, their surfaces and the microscopic spaces that exist between sutures or staples[44,47].

iv) Resistant to bacterial colonization. Dextrins have antibacterial properties that are useful for the protection of anastomosis where "micro leaks" could occur between the microscopic spaces that exist in sutures or staples, mainly discharges of secretions and bacteria.

v) Biodegradable and safe. Although the adherent strength of dextrins can persist for many weeks or months in the external atmosphere, the human body has the capacity to metabolize them and to turn them into simple carbohydrates that are absorbed without any adverse consequence. The FDA and the National Research Council have indicated that approvability of biological adhesives will be enhanced where a minimum amount of solvent is used and the polymer is biodegradable.

Therefore, another aspect of the present invention is to provide a formulation based on a dextrin as an effective, safe, biological adhesive, with appropriate adherent strength for biomedical applications, particularly those that involve smooth tissues. More specifically, the present invention is directed to useful compositions that temporarily protect anastomosis to eliminate dehiscences to the maximum, and that, in addition, can serve as an adhesive for inguinal prosthesis in hernia operations and for occluding certain types of fistulas.

In the present invention, another aspect of the composition based on dextrin is to combine a dextrin with other agents that confer additional desirable characteristics and also avoid adhesions with the surrounding organs and structures, for example, an interface of cellulose or collagen can be included to avoid such adhesions.

BRIEF DESCRIPTION OF THE DRAWINGS

Various features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
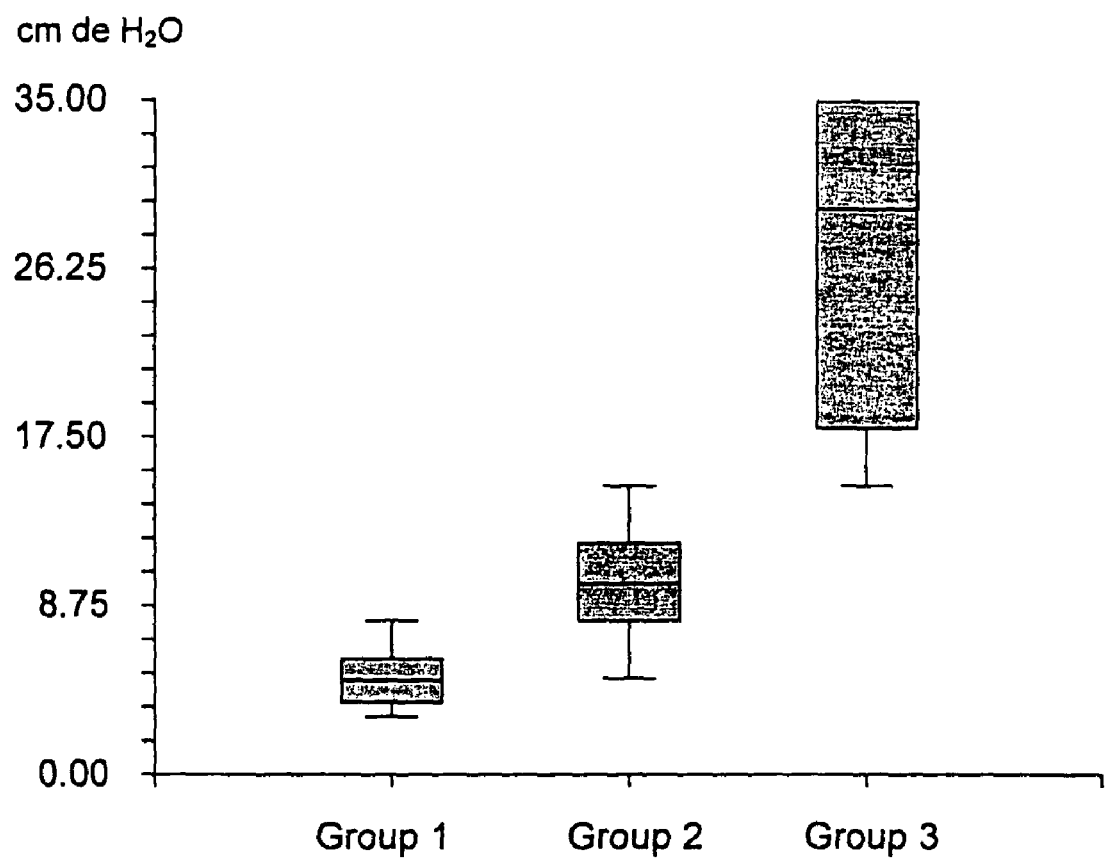
FIG. 1 shows the results of a test to determine the hydraulic pressure required to produce a leak ("bursting pressure") in suture lines in the rat's intestine, Phase 1. (Test ANOVA)

The term "dehiscence" used presently includes any defect or failure of the anastomosis in the gastrointestinal, respiratory, urinary systems, etc., that can produce leakage of secretions and bacteria through this defect, with very serious and frequently lethal consequences. This statement is not to be considered limitative but rather illustrative of some of the applications of the biological adhesive of the present invention to eliminate dehiscences of anastomosis to the maximum.

The terms "adhesive formulation" and "adhesive" are used in an interchangeable indistinct way and mean any biological adhesive that offers protection.

The adhesive formulation of the present invention is biodegradable, non-toxic, safe and effective, and has the capacity to provide temporary protection of anastomosis for several days, particularly during "the critical days" in order to enhance healing. It must be understood clearly that the adhesive formulation of the present invention is not a substitute for good surgical techniques, but an additional element of protection.

In an aspect of the present invention, the adhesive formulation is constituted mainly by a natural product, and which is easy to use and inexpensive. The formulation has demonstrated to have very useful properties in experiments made in minor and major animal species, and is very well tolerated and biologically degraded, (depending on the physico-chemical mixture and concentration of additional components), after the 10th post operative day without any collateral or undesirable effect.

In another aspect of the invention, the adhesive formulation can be used with such similar results for temporary fixation of prosthesis in inguinal hernia operations (and others as well). In addition, the adhesive can be used to facilitate the closing of some digestive fistulas or fistulas of other organ systems, if there is no obstruction or active suppuration.

In agreement with the previous statement, the biological adhesive of the present invention has the characteristics and properties, such as, it allows effective temporary protection of the anastomosis between 2° and 10° postoperative days, is not toxic, and does not produce adverse reactions or risks of transmission of infectious agents. It minimizes the demands on surgical resources and time, and demonstrates superior biocompatibility. In addition, the biological adhesive of the present invention offers improved convenience and permanence compared to formulations presently available. Also, the inventive formulation, promotes treatment of the patient, and reduces hospital stays and/or medical supervision. Additionally, the strength of adhesiveness of the present invention does not affect the normal physiological functions of the digestive system and other organ systems, where it is applied.

An important advantage of the inventive biological adhesive is that the adhesive effectively can protect the anastomosis during the crucial time period between the 2nd and $8^{th}$ postoperative days. It is during this time period that the anastomosis is particularly week because collagen deposition and development of new tissue bridges ($2^{nd}$ phase of healing process) has yet to occur.

Another important advantage of the inventive biological adhesive is its non-toxic nature, thereby allowing the formulation to be used as an internal biological adhesive for anastomosis, without the safety concerns associated with, for example, biological adhesives obtained from fibrin that are very expensive, and complicated to use. Additionally, in this time of cost containment, the biological adhesive of the present invention is extremely inexpensive.

Once again, this biological adhesive contains a material of fundamentally natural origin that has the property to adhere to tissues and/or live structures (call "bio-adhesion") for a determined period of time. So, in order for this "bio-adhesion" to be effective, an intimate contact between the adhesive material and the receiving tissue must exist. Preferably, the adherent material makes not only direct contact with the surface of the tissue and/or live structure, but also penetrates into the hollows or grooves of the receiving tissue so that mechanical, chemical and/or electrostatic connections or unions or links are formed. Of course, the adherent property of the material will be affected by certain factors, such as the physical and chemical conditions where it is applied[44-47].

The biological adhesive of the present invention includes a dextrin, an adhesiveness modifier agent and an antibiotic. Each one of the components of the biological adhesive is present in suitable amounts to provide the characteristics and properties previously mentioned.

The term "dextrin" as it is used in the present invention means a glucose polymer that forms from starch hydrolysis and which has glucose units connected by α-1,4 or α-1,6 links. As it is known, dextrins are hydrosoluble polysaccharides (dextro-rotatory polymers) of diverse molecular weight and chemical structure, obtained from partial hydrolysis of starch. In biological systems, this conversion takes place by the enzymatic action of α-glycosidases or dextrinases, but industrially the conversion is carried out by means of acids, heating or both. The dextrins are not susceptible to fermentation, and have antibacterial properties. Dextrins exist with a high or low level of conversion (hydrolysis). In general, the former are more hydrosoluble, whereas with greater solid concentration (for example, borax, as discussed below) the greater the adhesiveness. Dextrins also exist naturally in some vegetables during the process of germination and maturation. The dextrins also can be classified as white dextrins (greater viscosity), yellows (greater adhesiveness) and "British gum", which have a high degree of conversion.

Preferred dextrins for use in the formulation of the biological adhesive of the present invention are those that exhibit a viscosity of 12,000-33,000 cp (for example, 15,000-32,000 cp, or 12,000-25,000 cp, or 15,000-25,000 cp, or 15,000-18,000 cp, or 30,000-32,000). In preferred embodiments of the invention, a dextrin such as maltodextrin is used at one of two different concentrations: (1) maltodextrin with a viscosity 12,000-18,000 cp (such as 15,000-18,000 cp), especially 12,000-16,000 cp, wherein the resultant composition is in the form of a suspension which is easy to apply and has the above mentioned properties, and (2) another maltodextrin with a higher viscosity (e.g., 30,000-32,000 cp), wherein the resultant composition is in the form of a paste. These viscosity ranges are based on the formulation containing dextrin, the carrier (e.g., water), and an adhesiveness modifier (e.g., borax or zinc oxide). It is believed that the antibiotic will have little effect on the viscosity.

In embodiment (1) mentioned above, the resultant adhesive composition needs between about 10-12 minutes to cure (based on animal tests) and produce the desired adhesiveness. In embodiment (2) mentioned above, the resultant adhesive composition has a higher concentration of zinc oxide and/or borax and thus requires only 5-6 minutes to cure (based on animal tests), but due to this characteristic the composition is applied as a paste and produces minimal adhesions to surrounding fatty tissues. As noted, the estimated curing times mentioned above are based on acute animal experiments wherein curing times were measured in the determination of the bursting pressure of a suture line. In clinical use in humans, the adhesive formulation will obviously be allowed to sufficiently cure and will remain in place for several days protecting the anastomosis, or affixing the prosthesis, or occluding the fistula, and then later on will be metabolized.

In the formulation, the dextrin is used in the form of a mixture or suspension with a pharmaceutically acceptable carrier/excipient such as water. This mixture/suspension can have a solids content of, for example, 45-75%, preferably 55-70, especially 60-68%.

The addition of some solids to the dextrin, for example, borax hydroxide, iron, zinc, etc., modifies certain properties of the dextrins such as viscosity, drying time and adhesiveness.

The dextrins have been used commercially in diverse forms for several decades, like as adhesives for paper, pasteboard, packages, etc. In spite of daily frequent contact with the skin and human digestive system, no toxic effects are known. In fact, certain types of dextrins, for example, malto-dextrins, are used for the manufacture of beer.

The selection of the dextrin as the main component of the present inventive adhesive formulation or biological glue—for use as safe, temporary protection of anastomosis of the gastrointestinal, respiratory, urinary systems, and to fix the prosthesis of hernia operations among other clinical uses—is based on several months of extensive tests with diverse products, on a large number of inorganic materials and, later on, derived from experimental work in minor and major animal species, under a strict research protocol. As mentioned previously, the selection of dextrins is based, in addition, on the following properties and/or characteristics:

Non Toxic for Humans

After several decades of commercial use of dextrins in adhesives, with daily, direct contact to the skin, the mucosa and the lips, etc., no toxic or adverse effects are known. In addition, an extensive literature search does not reveal any evidence of toxicity. High-residue foods such as complex carbohydrates, including dextrins and similar compounds, are ingested daily by human beings without any toxicity, and related compounds (maltodextrins) are used in the production of the beer. They are also used in the manufacture of capsules, etc.

Recently, sulphated dextrins have been used successfully in humans by a group of investigators at Hammersmith Hospital of London, wherein sulphated dextrins were administered intraperitoneal to patients with Kaposi's Sarcoma, since they have the property to inhibit the angiogenesis in this tumor. A favorable response by its use was observed without undesirable effects, i.e., they were well tolerated, even in these very sick patients[48].

Use of icodextrins is common in peritoneal dialysis in concentrations from 4 to 7%[49,50]. An example of the use of icodextrins is disclosed in U.S. Pat. No. 6,770,148, issued 3 of Aug. of 2004, and entitled "Solution for peritoneal dialysis that contains modified icodextrins". Other groups recently have used intraperitoneal icodextrins in women with reproductive problems. Apparently, pelvic adhesions decreased and no collateral or toxic effects were observed, only a single report of a minor allergic reaction[51,52].

Cyclodextrins have special properties that allow them to improve the stability, solubility and bioavailability for oral absorption of some drugs, and they are used accordingly. Cyclodextrins are degraded enzymatically in the digestive lumen, mainly in the colon, and no toxic effects are known. Due to the mentioned properties, use of cyclodextrins intravenously is under investigation at the present time with great interest[53].

Maltodextrins also are used orally in solutions for rehydration, and in pill manufacture, etc., without any reports of toxicity.[54]

Finally, it must be remembered that a compound closely related to dextrin from a biochemical point of view, that is, a modified starch (hydroxy-starch), is frequently used intravenously in emergency situations in humans as a volume-expander.[55]

In the studies discussed below, maltodextrin is used. Maltodextrin, derived from vegetables and, in industrial processes, mixed with borax (2-4%), has been used as glue commercially for decades. However, since other dextrins share similar physic-chemical properties, the applicant considers that they can also be used for similar purposes in accordance with the invention. In fact, they are used frequently in humans in different medical applications successfully. Maltodextrins are non-toxic and are used commercially in the food-processing business. They are ingested daily in many places in the world and are easily digested in the GI tract to form glucose.

Resistant to Bacterial Invasion

Dextrins have antibacterial properties. This property is of particular importance in biological adhesives for protection of anastomosis where the "micro leaks" of secretions and bacteria between microscopic spaces of sutures or staples can occur, where germs make contact with organs and intraperitoneal and/or intrathoracic structures, or with foreign bodies like a prosthesis with very serious consequences.

High Penetration in Hollows or Grooves

The application of dextrins in porous substrates such as paper and cardboard, has demonstrated their high capacity to penetrate hollows or grooves on and through surfaces to which they are applied. Therefore, penetration into grooves or hollows of the receiving tissue is an important property of dextrin, with respect to microscopic defects in the anastomosis (denominated "micro leaks" of liquids and bacteria present in the lumen of the digestive system).

High Resistance to the Humidity

Adhesives based on dextrin exhibit a high environmental resistance to humidity. This characteristic is important because the adhesive can thus be applied in an internal cavity with normally high humidity. Also, the dextrin will work as an adhesive at the human body temperature.

Biodegradable

Although in an external environment the strength or force of the adhesion can persist for many weeks or months, dextrin's force or strength of adhesion in the human body is temporary, due to the capacity of living human tissues to metabolize the adhesive. The resulting products are simple carbohydrates that are eliminated or absorbed without adverse consequence. When metal oxides are used to increase the viscosity and the tack, the adhesive of the present invention can be observed to adhere to the intestinal segment for up to 3 weeks later. In this case, if an interphase is not used, some adhesions to the neighboring intestinal loops may occur.

Very Inexpensive

The cost of the adhesive according to the invention is approximately, $2,000.00 pesos ($ 200 USD) per 60 kg.

Preferred dextrins (in admixture with a pharmaceutically acceptable carrier/excipient such as water) for use in the formulation of the biological adhesive of the present invention are those that exhibit a viscosity of 12,000-33,000 cp such as 15,000-32,000 cp, or 15,000-25,000 cp, 15,000-18,000 cp, or even 30,000-32,000 cp (higher zinc oxide concentration). The latter ones with higher zinc oxide and/or borax content (this due to the fact that the industrial production includes borax to increase viscosity and tack), can also be used, but topical application requires an extra 2 minutes for it is a paste. The dextrin-water mixture (having a solids content of, for example, 45-75%, preferably 55-70, especially 60-68%) is present in the formulation of the biological adhesive in an amount of about 80%-97% (e.g., 90-97% or 80%-95%), preferably 92%-96%, by weight of the total formulation.

In the less viscous form (viscosity of, e.g., 12,000-16,000 cp), the solid content of the dextrin/water mixture is, for example, 60-63%, and it has a pH of 8-9 with a tack time of about 10-14 min. This formulation works well at room temperatures (e.g., 20-30° C.), does not require heating and remains active for 6 months in a dry storage room. The more concentrated viscous forms having a viscosity of 30,000-33,000 cp, is in the form of a paste, also works well in room temperature of 20-30° C., and has a tack time of 4-6 min.

The adhesiveness modifier agent used in the biological adhesive of the present invention is preferably an insoluble metallic oxide powder. As it is known in the art, borax is used in industrial processes to modify the physical characteristics of dextrins such as, for example, viscosity, adhesiveness, solubility in the water, tack, etc. Nevertheless, the use of borax can produce adverse effects such as adhesion when it is in free direct contact with the intraperitoneal structures. It is known that diverse metal compounds such as calcium, iron, titanium, zirconium, and zinc can be incorporated into polymers to increase the capacity of the polymers to adhere to tissues. These metallic compounds preferably are insoluble in water and have an ionizable charge in the surface where they are used. Incorporation of the metallic compound into the polymer can be achieved by mixing with the polymer or by covering the polymer ("coating")[46,47]. Also, it is known that some polymers that contain metals actively adhere to tissues such as mesenteric, surrounding adipose tissue, a phenomenon we observed with very viscous dextrins (30,000 cp or higher) when the biological adhesive is placed in the peritoneal cavity without a patch or interphase of a biodegradable material.

Zinc oxide powder is a preferred adhesiveness modifier agent for use in the biological adhesive dextrin-based of the present invention. Zinc oxide has the approval of the FDA as a pharmaceutically acceptable additive and can be ingested by humans without adverse collateral effect. In addition, zinc oxide, due to its emollient, absorbent properties, among others, is daily used in an endless number of applications such as treatment of wounds, decubitus ulcers, "diaper rash" in babies, etc. As mentioned previously, zinc oxide when added to the polymer (dextrin) increases the biological adhesiveness of the polymer, its tack, and diminishes the drying time, thus improving the properties of the formulation as a biological adhesive to temporarily protect the anastomosis, or to fix a prosthesis used in hernia operations. With a higher viscosity, e.g., 30,000 cp (or higher), the biological adhesive is in the form of a paste which must be applied with, for example, a cotton tip applicator. Finally, zinc, as it is well known, is a very important ion in human metabolism and in the healing process.

The adhesiveness modifier agent is present in the biological adhesive of the present invention in a suitable amount to modify the adhesive strength of the adhesive in such a way that the biological adhesive remains temporarily in the anastomosis. In addition, the amount of adhesiveness exhibited by the biological adhesive is suitable to promote healing of the anastomosis. The adhesiveness modifier agent is present in the formulation of the biological adhesive in an amount up to about 19% by weight (e.g., 4-8% by weight), but preferably is about 2-6% by weight of the total formulation, and very preferably about 4 to 6% by weight of the total formulation. Also, the cost of zinc oxide is very inexpensive, similar to the cost of dextrin.

Because there is solid experimental and clinical evidence that extensive bacterial invasion interferes with the healing process everywhere, the adhesive formulation of the present invention includes an antibiotic, preferably to avoid problems associated with bacterial invasion. The inventor of the present invention has found that the preferred antibiotic agent for topical use is kanamycin due to its well-known efficacy when used topically in the surgical wounds but more importantly because it has been used safely and extensively inside the abdominal cavity.

It has been known for many years, that the topical use of intraperitoneal kanamycin in doses of 2-3 grams applied at the site of maximal bacterial contamination (for example, in the case of a perforated appendix, it is applied near the site of the stump) during surgery, may help prevent residual septic complications[56-58]. Recently, its successful use in topical form in the large incisions of bariatric surgery—known for high risk for infection—has been reported, without adverse effects[59,60]. Kanamycin, used clinically by the intramuscular route, in doses of from 1 to 2 g/day during 7 to 10 days, has demonstrated in time to be an effective and safe antibiotic. However, for the required antibiotic effects in the adhesive formulation of the present invention, the antibiotic agent is used in amounts that do not interfere with the healing process. Preferably, the antibiotic agent is present in an amount of between 0.1 and 1% by weight of the total formulation (for example, of 100 to 125 milligrams). In a particularly and preferable modality of the invention, the antibiotic agent is present in amounts of between 0.2 and 0.5% in weight of the total formulation (for example, of 250 to 500 milligrams single dose in the topical application).

Other antibiotics are also suitable for use in the inventive composition such as a 1$^{st}$ generation cephalosporins like cefazolin. This popular and inexpensive antibiotic is used topically and subcutaneously to prevent incisional infections. Ann R Coll Surg Engl. May 1978; 60(3):243-5.). Gentamycin, Clindamycin and Vancomycin are also suitable antibiotics. These agents are being used topically with collagen with good results externally. (Phinney, R. B., Schwartz, S. D., Lee, D. A., Mondino, B. J.: Collagen shield delivery of gentamycin and vancomycin. *Archives of Ophthalmology,* 1988. 106 pp. 1599-1604).

The formulation may also pharmaceutically acceptable adjuvants and excipients. In addition, the formulation may contain further active agents. For example, the formulation may contain growth factors, i.e. substances that in very small amounts can be placed in wounds to stimulate development of new vessels, namely angiogenesis which is vital for the development of new tissue such as collagen. Such growth factors are derived mainly from macrophages present in the wound along with different types of cytokines in the initial phase of the healing process and some of them are the platelet one (PDGF), a vascular GF (VEGF), Keratinocyte GF (wounds), etc. (te Velde E A, Voest E E, van Gorp J M, Verhemm A, Hagendoorn J, Gebbink M F, et al., Adverse effects of the antiangiogenic agent angiostatin on the healing of experimental colonia anastomoses. Ann Surg Oncol 2002; 9:303-9; Bennet N T, Schultz G S, Growth factors and wound healing: Part II. Role in normal and chronic wound healing. Am J Surg 1993; 166:74-81).

A further example of an additional active agent is arginine. Arginine is an amino acid that plays a role in cell division, healing of wounds, improving immunity to illness, etc. It is used by the body to make nitric oxide, a substance that dilates blood vessels which plays an important role in wound healing (Rizk M, Witte M B, Barbul A. Nitric oxide and wound healing. World J Surg 2004; 28:301-6).

L. P. Fielding el al described in the British Medical Journal the results of a large multicentric study in colo-rectal cancer surgery in which the concept of mini-leaks—which occur at a much higher rate than previously thought in these anastomosis—is supported, and where the clinically relevant anastomotic leaks produced three times as much mortality, expense and hospital stay[62,63]. Other reports have demonstrated that although an anastomosis that tested well during the operation and did not show a visible air or fluid leak (so-called physical impermeability), that does not mean that is completely sealed to prevent passage of bacteria and secretions into the peritoneal cavity (biological impermeability) as shown by A. Zaporozhets[64]. In fact, mini-leaks not clinically relevant are shown in patients when radio-opaque enemas are administered in the first 7 days postoperatively and many of these leaks do not produce peritonitis. However, this may explain why some patients have a more torpid postoperative course, others develop a pericolic abscess later, and in some others an extensive adhesive process surrounds the area of the anastomosis.

In accordance with a method aspect of the invention, once an anastomosis has been finished and duly tested for its integrity, the biological adhesive of the present invention is applied, for example with a sterile cotton tip applicator, in a sufficient amount to cover completely the area over the suture line. Then, a patch (an interphase) of cellulose or collagen is preferably applied with sterile technique to cover the area in a way that adhesions with surrounding structures are avoided. Although in chronic animal experiments this method provides survival in defects not sutured, in humans once the anastomosis is completed and tested, the biological adhesive of the present invention is preferably applied with an interphase to reinforce the suture lines, to promote healing during the critical period of several days when the anastomosis is held only by sutures and/or staples, in an area of acute inflammation, with no collagen deposition, without any intrinsic strength per se, and in a manner which will prevent the occurrence of a dehiscence and/or mini-leaks. This is a very advantageous aspect of the inventive adhesive and method. A similar method can be used to fix the prosthesis in inguinal hernioplasties.

In another aspect of the invention, the method of application of the biological adhesive based on dextrin can include, in addition, a patch, an interphase of sterile cellulose or collagen as a patch, in order to avoid adhesions with the surrounding organs and structures. These patches that constitute the interphase are used very frequently in neurosurgery, orthopedic surgery, general surgery, etc. as haemostatic agents. This interphase is reabsorbed in 3 to 6 days.

In another modality of the present invention, some fistulas of different etiology (e.g., gastric bypass) can also be closed from their orifice of origin by endoscopic procedures using the biological adhesive of the present invention instead of re-operating on the patient, if the clinical situation so permits.

The entire disclosure of all applications, patents and publications, cited above and below, are hereby incorporated by reference.

EXAMPLE

The following examples are provided solely to illustrate the present formulation, and are not intended to limit the scope of the invention.

A biological adhesive of the present invention was prepared in the following way: Approximately 93-94% by weight of dextrin, 1-2% borax (industrially used in the production of maltodextrin), 0.4-0.5% formaldehyde (used in industrial formulations as an additive to make the adhesive more water-resistant and to slow bacterial growth during storage), 5% by weight of adhesiveness modifier agent, and 0.5% by weight of the antibiotic agent are added to a small container. The presence of borax and formaldehyde are not required in the inventive formulation. Borax and formaldehyde are typically present in industrial produced maltodextrin. The components are vigorously mixed together for about 15 minutes using a mechanical agitator, until a homogenous mixture or paste is formed. If a homogenous mixture does not form, the mixture is warmed up until a temperature of, for example, between 23 to 30° C. to reduce the viscosity of the dextrin and allow the adhesiveness modifier agent and antibiotic agent to properly mix with the dextrin. The antibiotic can also be added later separately, for example, just before the adhesive formulation is applied to the suture line.

Research Support of the Invention

Protocol Approved by the School of Medicine, Universidad Anahuac, Mexico City, February 2005

Phase 1

In the first phase, 250 to 300 g rats were used in acute experiments, in which, after an abdominal midline incision, 2 intestinal loops of 10 cm each were isolated with 4-0 silk sutures. Then, a 3 mm incision was made in the antimesenteric edge, sutured with a single stitch of 6-0 silk. At the ends of the closed loop, a 16 gauge intravenous catheter was introduced and connected "in a Y" fashion to a central venous pressure manometer and physiological serum was injected with a syringe, a method similar to the one described by Arnold et al.[61]. FIG. 1 graphically shows the hydraulic pressure required to produce leakage in the sutured line in each group (1, 2 and 3). In group 1 the hydraulic pressure necessary to produce leakage ("bursting pressure") in the sutured area, ranged from 3-5 cm of water, whereas in group 2 in which a patch of cellulose or of collagen of 3 $mm^2$ had been added, the hydraulic pressure necessary to produce such a leak increased to 5-8 cm of water. In group 3 the biological adhesive of the present invention was added to the patch, which was let to dry 15 minutes. The pressures that were required to produce the leakage of liquid in group 3 increased to 18-45 cm of water, which was a statistically significant difference p: 0.05. (test ANOVA). In each group 28 measurements were made.

In conclusion, in this phase 1, the biological adhesive of the present invention had a protective effect on the suture line, as demonstrated by a much higher hydraulic pressure being required to produce fluid leakage in group 3, as compared to groups 1 and 2.

Phase 2:

In sub acute experiments and using sterile techniques, in 250 to 300 g rats, a 2 to 3 cm midline vertical incision was made and an intestinal loop was exteriorized. An incision of 3 mm was made in the antimesenteric edge. In group 1, a patch of cellulose or collagen of 3 $mm^2$ was placed over the incision but without any suture or adhesive. In group 2, a patch of cellulose or collagen of 3 $mm^2$, to which an effective amount of the adhesive of the present invention was applied on the surface, was placed over the incision. The abdominal incision was sutured using 4-0 polidioxanone in two layers. The rats were returned to their cage and the survivors were observed for three weeks. The survival rate in group 1 was 52%, whereas in group 2 the survival rate was 75%.

Figure 2:
FIG. 2 is a microphotograph of a segment of the intestine of a rat from group 1 that died in 3 days, in which the defect was covered with a patch, but not an adhesive or suture, Phase 2.
Figure 3:
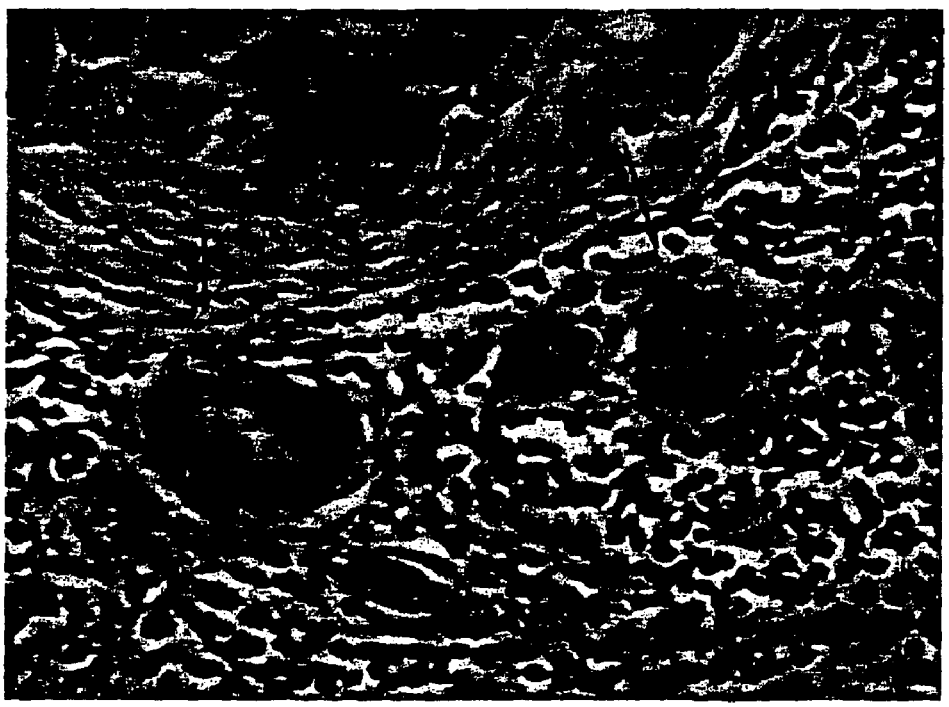
FIG. 3 is a microphotograph of a segment of the intestine of a rat from group 1 that survived 3 weeks, in which the defect was covered with a patch but not adhesive or suture, Phase 2.
Figure 4:
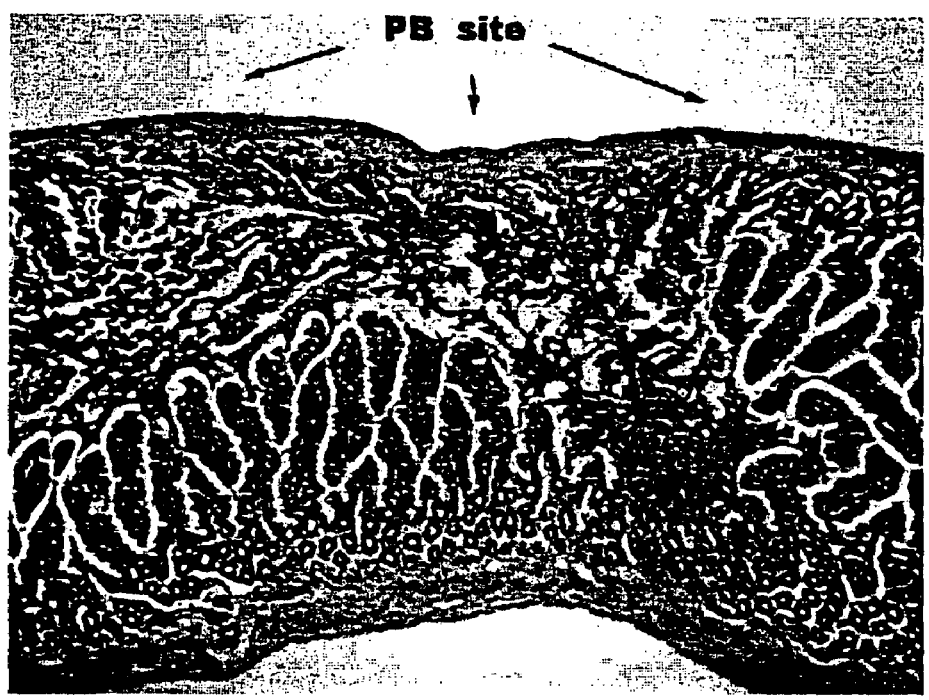
FIG. 4 is a microphotograph of a segment of the intestine of rat from group 2, in which a patch was placed with the biological adhesive of the present invention, Phase 2.

The purpose of phase 2 was to observe the tissue reaction, both macroscopically and microscopically, in the intestinal tissue. As can be seen in FIGS. 2 and 3, in the case of rats of group 1 that died in the first three days due to peritonitis, the well-known phenomena of intense inflammatory reaction, cellular infiltrate and even intestinal defect were observed (FIG. 2). In the necropsies of the surviving rats in the same group, from the macroscopic point of view, multiple adhesions were observed to the abdominal wall and to the surrounding intestinal loops with fibrosis, and the presence of giant cells was also observed. In 2 cases large parietal abscesses were seen (FIG. 3). On the other hand, in the surviving rats of group 2, it was impressive to observe an intact serous surface, and it was difficult or impossible to determine the site where there had been a laceration and patch with adhesive of the present invention. Microscopically, the intestinal wall healed normally (FIG. 4), and in these animals no inflammatory reaction or giant cells were observed, which makes us conclude that the adhesive of the invention is very well tolerated and disappears after several days. As for the cellulose and/or collagen patch used frequently in general surgery, orthopedic surgery, neurological surgery, etc., it is known that its reabsorption happens in the first 3 to 5 days after its application.

As a result of the experimental observations in phase 2, it is concluded that the biological adhesive of the present invention was very well accepted by intestinal tissues of the rat and sometimes it was impossible to determine with certainty the exact site of the application of the patch with adhesive in the site of the injury.

Phase 3:

The observations made of Phases 1 and 2, were extended and applied to dogs using sterile techniques. Preoperatively, 1 g intramuscular of a second generation cephalosporin was applied. The technique involved making a 6 cm vertical midline incision under the xyphoid appendix, and, by means of careful gastric traction, the duodenum was exteriorized. Then, a 5 to 6 $mm^2$ laceration was made in the antimesenteric edge using a fine haemostatic clamp 4-5 cm distal to the pancreatic duct. Then, a 3 cm 2 patch of cellulose or collagen was applied with the adhesive of the present invention over the laceration. After 12 min., the duodenum was returned to its normal position, that is, the laceration was not sutured, and a patch with the adhesive was applied over the defect. The incision was then closed with 2-0 polidioxanone, a continuous suture in two separated layers.

Figure 5:
FIG. 5 is a photograph showing the macroscopic aspect of the duodenum three weeks after placing a patch with adhesive in a dog, Phase 3.
Figure 6:
FIG. 6 is a microphotograph showing the microscopic evaluation of the duodenal injury of a dog after three weeks, Phase 3.

The animals were observed during 3 weeks and were sacrificed with an intravenous dose of sodic pentotal. In two occasions the autopsy took place 2 months later. Of a total of 28 dogs, 3 died in the first 72 hours, the first 2 and 1 with an extended laceration. The macroscopic evaluation, in four surviving animals demonstrated minimum adhesions to fatty tissue. But, in the rest of the animals, at the site or the injury, only a small scar was observed (FIG. 5). The microscopic sections, shown in FIG. 6, like in the previous phase 2 in rats, revealed a normal healing process of the intestinal wall, without inflammatory reaction or giant cells.

Phase 4:

Both in rats and in dogs the suture lines and the defects created in the duodenum and distal intestine not sutured but patched, were tested with hydraulic pressure at 8 days and the results were again the same: The biological adhesive of the present invention provided more strength to prevent "bursting" of the suture lines or defects as compared to the sites sutured and/or patched without adhesive formulation.

In conclusion, the temporary biological adhesive of the present invention protects the suture lines based on the fact that a greater hydraulic pressure in Phase 1 is required to produce leakage of liquid in the suture line when the patch and adhesive were placed. This results in a greater survival rate in rats as shown in Phase 2. In Phase 2, there was an intense inflammatory reaction and cellular infiltrate in rats which died soon (Phase 2, group 1: patch alone). A chronic inflammatory process with giant cells was observed in surviving rats (Phase 2, group 1: patch alone), as compared with a normal healing process when the patch was applied with the adhesive of the present invention (Phase 2, group 2: patch with adhesive). In Phase 3, involving dogs with a very serious, lethal injury in the duodenum, where it is known that pancreatic and intestinal secretions exist, most animals survived and similar findings to those observed in rats were present, namely a normal healing process in the duodenal wall and site of the injury. All of these results are proof that the adhesive of the present invention produces the necessary seal by its adhesive properties. In Phase 2 and in Phase 3, the macroscopic and microscopic findings were similar: the biological adhesive is very well tolerated by the intestinal tissues, external adhesions practically do not exist, and histological signs of inflammation or giant cells were not observed. In Phase 2, it was practically impossible sometimes to determine the site of the injury in the intestine of the rat, and in the dogs in Phase 3, only a small scar existed. Microscopically, an inflammatory reaction or a foreign body type of reaction did not exist. All of these results lead to the conclusion that the adhesive of the present invention is not only very well tolerated, but is also biodegraded in 5 to 8 days after the application, precisely the critical period of intestinal healing in the case of the mentioned gastrointestinal anastomosis.

Finally, in both, rats and in dogs using a similar experimental method of Phases 1 and 3 at 8 days postoperatively, equal results were found: greater hydraulic pressures were required to produce leaks ("bursting pressure") in the suture lines and sites of defects patched when the adhesive of the present invention was applied.

Although a form of specific accomplishments of the present invention have been described in detail with the previous examples, it must be stated that the present invention and formulations, are susceptible of diverse modifications and alternative forms of use, without separating them from the spirit and reaches of the present invention. Therefore, the intention is not to limit the invention and method herein described, but instead, to cover all the equivalent and/or alternative modifications that fall within the reaches of the invention as it calls to each other by the annexed claims.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

REFERENCES

[1] P. Schauer, Gastric bypass for severe obesity: Approaches and outcomes, Surgery for Obesity and related Diseases, 2005 1-3, 297-300;

[2] H. Buchwald, Consensus Conference Statement: Bariatric surgery for morbid obesity: Health implications for patients, health professionals, and third-party payers Surgery for Obesity and related Diseases, 2005, 1-3, 371-381;

[3] C. Jensen y cols, The costs of non-surgical and surgical weight loss interventions: Is an ounce of prevention really worth a pound of cure?, Surgery for Obesity and related Diseases, 2005, 1-3, 353-357;

[4] National Institutes of Health consensus statement on "Gastrointestinal Surgery for Severe Obesity", 1991, March, Washington D.C.;

[5] M. Gagner et al., Chapter 26, Section III, Laparoscopic Roux-en-Y Bypass for morbid obesity, in: "Laparoscopic Surgery" 2003, Eds. J. Cueto, M. Jacobs, M. Gagner, Ed. McGraw-Hill, New York;

[6] R. E. Brolin, Postoperative complications in the context of risk: benefit, Surgery for Obesity and related Diseases, 2005, 1-3, 343-347;

[7] R. Gonzalez et al., Anastomotic Leaks after Laparoscopic Gastric Bypass, Obesity Surgery, 2004, 14-10, 1299-1307;

[8] R. S. Baker et al., The Science of Stapling and Leaks, Obesity Surgery, 2004, 14-10, 1290-1298;

[9] A. Csendes et al., Conservative Management of Anastomotic Leaks after 557 Open Gastric Bypasses, Obesity Surgery, 2005, 15-9, 1252-1256;

[10] Truong S et al., Results after endoscopic treatment of postoperative upper gastrointestinal fistulas and leaks using combined Vicryl plug and fibrin glue. Surg. Endosc. July 2004; 18(7):1105-8;

[11] J. A. Sapala et al., Anastomotic Leak Prophylaxis Using a Vapor-Heated Fibrin Sealant: Report on 738 Gastric Bypass Patients, Obesity Surgery, 2004, 14, (1), 35;

[12] S. A. Shikora, The Use of Staple-Line Reinforcement During Laparoscopic Gastric Bypass, Obesity Surgery, 2004, 14-10, 1313-1320;

[13] G. Meng et al., Use of Fibrin Sealant in Laparoscopic Gastric Bypass for the Morbidly Obese, Obesity Surgery, 2004, 14-10, 1321-1327;

[14] Plasencia et al., Laparoscopic Colectomy, Chapter 41, Section VI, Large Bowel Surgery, en: "Laparoscopic Surgery" 2003, Eds. J. Cueto, M. Jacobs, M Gagner, Ed. McGraw-Hill, New York;

[15] M. Franklin et al., Colonic Resection in the Treatment of Colorectal Carcinoma: Multicentric Study with Prospective Comparison of the Traditional and Laparoscopic Methods, Chapter 42, Section VI, Large Bowel Surgery en "Laparoscopic Surgery" 2003, Eds. J. Cueto, M. Jacobs, M. Gagner, Ed. McGraw-Hill, New York;

[16] Appendix: Conclusions of the Consensus of the European Association for Endoscopic Surgery Experts Opinion Conference on Colonic Cancer by Elective Surgery, Chapter 43, Section VI, Large Bowel Surgery, in: "Laparoscopic Surgery" 2003, Eds. J. Cueto, M. Jacobs, M. Gagner, Ed. McGraw-Hill, New York;

[17] T. Birdas et al., Laparoscopic Colectomy for Benign Disease, Chapter 44 Section VI Large Bowel Surgery, en: "Laparoscopic Surgery" 2003 Eds. J. Cueto, M. Jacobs, M. Gagner, Ed. McGraw-Hill, New York;

[18] R. Hartmann et al., Laparoscopic Surgery for Diverticular Disease, Chapter 45 Section VI, Large Bowel Surgery, en: "Laparoscopic Surgery" 2003, Eds. J. Cueto, M. Jacobs, M. Gagner, Ed. McGraw-Hill, New York

[19] E. Gòmez et al., Laparoscopic Management of Colonic Emergencies, Chapter 47, Section VI, Large Bowel Surgery, en "Laparoscopic Surgery" 2003 Eds. J. Cueto, M. Jacobs, M. Gagner, Ed. McGraw-Hill, New York;

[20] M. Franklin et al., Complications of Laparoscopic Colorectal Surgery, Chapter 93, Section XVII, Complications of Laparoscopic Surgery, in "Laparoscopic Surgery" 2003, Eds. J. Cueto, M. Jacobs, M. Gagner, Ed. McGraw-Hill, New York;

[21] H. Nelson, et al., A comparison of Laparoscopically assisted and open colectomy for colon cancer" The New England Journal of Medicine, May 2004:13;

[22] Walker K, Anastomotic leakage is predictive of diminished survival after potentially curative resection for colorectal cancer; Ann Surg, 2004, 240(2): 255-259;

[23] H. M. Schardey et al., "The prevention of anastomotic leakage after total gastrectomy with local decontamination. A prospective, randomized, double-blind, placebo-controlled multicenter trial." Annals of Surgery, February 1997; 225(2): 72-80;

[24] H. Schardey et al., Risk factors and pathogenic microorganisms in patients with insufficient esophagojejunostomy after gastrectomy, Zentralbl Chir. 1998; 123(1):46-52;

[25] J Cueto, A Weber. "Laparoscopic reoperations in the esophageal hiatus": Cemalettin Topuzly, Yaman Tekant. "Proceedings: Joint Euro Asian, Congress of Endoscopic surgery" 5th Annual Congress of The European Association for Endoscopic Surgery, Monduzzi Editore, pag. 133. Estambul, Turquía, 17 al 21 de Junio de 1997;

[26] J Cueto, O Rojas, D Garteiz, M Rodríguez, A Weber; "The efficacy of laparoscopic surgery in the diagnosis and treatment of peritonitis: Experience with 107 cases in Mexico City". Surgical Endoscopy, 1997; 11(4):366-370;

[27] J Cueto; "Peritonitis Séptica". Anales Médicos. Medical Association of The American British Cowdray Hospital, September 1978; 23: 130-142;

[28] J. Cueto, A Weber y F Serrano, Laparoscopic treatment of perforated duodenal ulcer Surgical Laparoscopy & Endoscopy, 1993; 3(3): 216-218;

[29] J. Cueto et al., The Laparoscopic Treatment of a Perforated Peptic Ulcer, Chapter 21, Section III, Gastric Surgery, en: "Laparoscopic Surgery" 2003, Eds. J. Cueto, M. Jacobs, M. Gagner, Ed. McGraw-Hill, New York;

[30] T. W. Kraus et al., Scientific evidence for application of topical hemostats, tissue glues and sealants in hepatobiliary surgery, Journal of the American College of Surgeons, March 2005;

[31] L. Ninan et al., Adhesive strength of marine mussel extracts on porcine skin, Biomaterials, 2003, 24, 4091-4099;

[32] K D Lillemoe, Does fibrin glue sealant decrease the rate of pancreatic fistula after pancreaticoduodenectomy? Results of a prospective randomized trial. J Gastrointest Surg. November 2004; 8(7): 766-72; discussion 772-4;

[33] J. Cueto, J Sánchez, O Toussaint, G Diehl and W Wolpert. "Cateterización percutánea y corrección de una fístula duodenal lateral." Revista Mexicana de Radiología, 1985; 39(2): 84-87;

[34] E. Felix, Laparoscopic Inguinal Hernioplasty, Chapter 62 Section IX, Hernia Surgery, en: "Laparoscopic Surgery" 2003 Eds. J. Cueto, M. Jacobs, M. Gagner, Ed. McGraw-Hill, New York;

[35] E. Felix et al., Complications of Laparoscopic Inguinal Hernia Repair, Chapter 94 Section XVII, Complications of Laparoscopic Surgery, en "Laparoscopic Surgery" 2003, Eds. J. Cueto, M. Jacobs, M. Gagner, Ed. McGraw-Hill, New York;

[36] N Katkhouda; A new technique for Laparoscopic hernia repair using fibrin sealant. Surg. Technol. Int. 2004; 12:120-6;

[37] M. Kapischke et al., Precoating of alloplastic materials with living human fibroblasts: a feasibility study Surgical Endoscopy, 2005, 19-6. 791-797;

[38] D. J. Mandley, J. F. Birch, S. L. Williams, P. J. Trotter, F. Wilkinson and G. A. Davies "Photon activated biological adhesives in surgery", *International Journal of Adhesion and Adhesives* 2000, 20(2), 97-102;

[39] J. F. Birch, D. J. Mandley, S. L. Williams, David R. Worrall, P. J. Trotter, F. Wilkinson and P. R. Bell "Methylene blue based protein solder for vascular anastomosis: an in vitro burst pressure study", *Lasers in Surgery and Medicine* 2000, 26, 323-329;

[40] U.S. Pat. No. 3,667,472 issued to Benjamin D. Halpern on Jun. 6, 1972, titled "Adhesive for Living Tissue";

[41] W Johnston et al., Fibrin glue v sutured bolster: lessons learned during 100 Laparoscopic partial nephrectomies. J Urol. July 2005; 174(1):47-52;

[42] C. Buchta, Impact of manufacturing, irradiation and filtration steps to bacterial contamination of autologous fibrin sealant. Biologicals. September 2004, 32(3): 165-9;

[43] M Kawamura, The sealing effect of fibrin glue against alveolar air leakage evaluated up to 48 h; comparison between different methods of application. Eur J Cardiothorac Surg. July 2005; 28(1):39-42;

[44] UNI-BOND 1100D MATERIAL SAFETY DATA SHEET, Uniplast, Inc., UNI-BOND 1100D DATE PREPARED: Jul. 8, 2000;

[45] CRC Handbook of food additives, T. E. Furia Ed., 1968, Cleveland, Ohio;

[46] Dimmitriu, Severian. *Polymeric Biomaterials Second Edition Revised Expanded*); Chapter 1: Polysacharides as biomaterials, New York, N.Y., USA: Marcel Dekker Incorporated, 2001. pp 3-30;

[47] Clinical Indications for Surgical Tissue Adhesives. William D. Spotnitz, Sandra Burks, and David Mercer, Clinical Applications of tissue adhesives, Kai Wise, Donald; Trantolo, Debra J.; Tissue Engineering and Biodegradable Equivalents: Scientific and Clinical Applications, (Eds.) Journal of Controlled Release Volume 92, Issue 3, Oct. 30, 2003, Pages 399-400, Marcel Dekker Incorporated, New York, 2002, pp. 652-660;

[48] M. Thornton, Anti-Kaposi's Sarcoma and Antiangiogenic Activities of Sulfated Dextrins Antimicrob Agents Chemother. October 1999; 43(10):2528-33;

[49] KATHRYN J WIGGINS, MARKUS RUMPSFELD, SOPHIE BLIZZARD and DAVID W JOHNSON. Predictors of a favourable response to icodextrin in peritoneal dialysis patients with ultrafiltration failure, Nephrology, February 2005, Volume 10, Page 33;

[50] E. M. Peers, C. B. Brown and Adept Adhesion Study Group Effectiveness of 4% Icodextrin in a Pivotal Adhesion Reduction Trial in the USA•ABSTRACT *Fertility and Sterility*, Volume 84, Supplement 1, September 2005, Page S155;

[51] Satish Jayawardene MRCP[a], Nikant Sabharwal MRCN[a] and Katrina Cooney RCN[a], Allergic reactions to the polymeric glucose-based peritoneal dialysis fluid icodextrin in patients with renal failure; David Goldsmith FRCP[a]; The Lancet, Volume 355, Issue 9207, 11 Mar. 2000, Page 897;

[52] Petrousjka van den Tol PhD, Sander ten Raa MD, Helma van Grevenstein MD, —Richard Marquet PhD, Casper van Eijck PhD and Hans Jeekel PhD; Icodextrin reduces postoperative adhesion formation in rats without affecting peritoneal metastasis; Surgery, Volume 137, Issue 3, March 2005, Pages 348-354;

[53] S. Almeida Prieto, J., Blanco Méndez and F. J. Otero Espinar; Starch-dextrin mixtures as base excipients for extrusion-spheronization pellets, European Journal of Pharmaceutics and Biopharmaceutics, Volume 59, Issue 3, April 2005, Pages 511-521;

[54] el-Mougi M, Hendawi A, Koura H, Hegazi E, Fontaine O, Pierce N F; Efficacy of standard glucose-based and reduced-osmolarity maltodextrin-based oral rehydration solutions: effect of sugar malabsorption. Bull World Health Organ. 1996; 74(5):471-7;

[55] Cornelius Jungheinrich, MD*, Roland Scharpf, PhD*, Manfred Wargenau, PhD, The Pharmacokinetics and Tolerability of an Intravenous Infusion of the New Hydroxyethyl Starch 130/0.4 (6%, 500 mL) in Mild-to-Severe Renal Impairment, Anesthesia Analgesia 2002; 95:544-551;

[56] Nelson J L, Kuzman J H, Cohn I Jr, Intraperitoneal lavage and kanamycin for the contaminated abdomen. Surg Clin North Am. December 1975; 55(6):1391-5;

⁵⁷Yelon J A, Green J D, Evans J T, Efficacy of an intraperitoneal antibiotic to reduce the incidence of infection in the trauma patient: a prospective, randomized study. J Am Coll Surg. June 1996; 182(6):509-14;

⁵⁸Gorman T, Eisele G, Bailie G R, Intraperitoneal antibiotics effectively treat non-dialysis-related infections. Perit Dial Int. July-September 1995; 15(6):283-4;

⁵⁹J. W. Alexander, Invited Commentary, Wound Infections in the Morbidly Obese, Obesity Surgery, 2005, 15-9, 1276-1277;

⁶⁰J W. Alexander et al., Prevention of Deep Wound Infection in Morbidly Obese Patients by Infusion of an Antibiotic into the Subcutaneous Space at the Time of Wound Closure, Obesity Surgery, 2004, 14-7, 970-974;

⁶¹W. Arnold et al., A Comparison of Burst Pressure Between Buttressed Versus Non-Buttressed Staple-Lines in an animal Model, Obesity Surgery, 2005, 15-2, 164-171.

⁶²Fielding L P, Stewart-Brown S, Blesovsky L, Kearney G., Anastomotic integrity after operations for large-bowel cancer: a multicentre study. British Medical Journal 1980:411-414.

⁶³L. P. Fielding, S. Stewart Brown, R. Hittinger, L. Blesovsky. Covering Stoma for Elective Anterior Resection of the Rectum: An Outmoded Operation? The American Journal of Surgery 1984; 147:524=530.

⁶⁴Zaporozhets A, Physical and biologic impermeability of intestinal sutures in the first twenty tour hours after operations on the gastrointestinal tract. Surgery 1992; 12:940=945.

The invention claimed is:

1. A non-toxic biological adhesive formulation for protecting and sealing anastomosis and suture lines in internal body cavities, said formulation comprising dextrin as a dispersion, at least one adhesiveness modifier agent comprising from 8 weight % to about 19 weight % zinc oxide powder based on the total weight of the formulation, and at least one antibiotic, wherein said formulation contains 80-97 weight % of said dextrin dispersion, and said dextrin dispersion contains 45-75 weight % solids, based on the total weight of the formulation, wherein said dextrin dispersion has a pH of 8-9 and a viscosity of 12,000-25,000 cp, wherein said formulation protects and seals anastomosis and suture lines in internal body cavities, and having a resistance to humidity to provide temporary protection of the anastomosis from at least the $2^{nd}$ to the $14^{th}$ post-operative days.

2. An adhesive formulation according to claim 1, wherein said formulation consists essentially of said dextrin, said at least one adhesiveness modifier agent, and said at least one antibiotic.

3. An adhesive formulation according to claim 1, wherein said dispersion is a dispersion of said dextrin in water.

4. An adhesive formulation according to claim 1, wherein said formulation contains 90-96 weight % of said dispersion, based on the total weight of the formulation.

5. An adhesive formulation according to claim 1, wherein said dextrin dispersion has a solids content of 60-68%.

6. An adhesive formulation according to claim 1, wherein said dextrin dispersion has a viscosity of 12,000-18,000 cp.

7. An adhesive formulation according to claim 1, wherein said dextrin dispersion has a viscosity of 15,000-18,000 cp.

8. An adhesive formulation according to claim 1, wherein said dextrin is a maltodextrin.

9. An adhesive formulation according to claim 1, wherein said at least one adhesiveness modifier agent further comprises an additional insoluble metal oxide.

10. An adhesive formulation according to claim 1, wherein said at least one adhesiveness modifier agent further comprises a calcium, iron, titanium, zirconium, cobalt, or additional zinc compound.

11. An adhesive formulation according to claim 1, wherein said at least one antibiotic is kanamycin.

12. An adhesive formulation according to claim 1, wherein said formulation contains 0.1-1 weight % of said at least one antibiotic, based on the total weight of the formulation.

13. An adhesive formulation according to claim 12, wherein said formulation contains 0.2-0.5 weight % of said at least one antibiotic, based on the total weight of the formulation.

14. An adhesive formulation according to claim 12, wherein said at least one antibiotic is kanamycin.

15. A non-toxic biological adhesive formulation for protecting and sealing anastomosis and suture lines in internal body cavities comprising dextrin as a dispersion, and at least one adhesiveness modifier agent comprising from 8 weight % to about 19 weight % zinc oxide powder based on the total weight of the formulation, wherein said formulation contains 80-97 weight % of said dextrin dispersion, based on the total weight of the formulation, and said dextrin dispersion contains 45-75 weight % solids, wherein said dextrin dispersion has a pH of 8-9 and a viscosity of 12,000-25,000 cp, and wherein said formulation protects and seals anastomosis and suture lines in internal body cavities.

16. A non-toxic biological adhesive formulation for protecting and sealing anastomosis and suture lines in internal body cavities, said formulation comprising dextrin as a dispersion, at least one adhesiveness modifier agent comprising from 8 weight % to about 19 weight % zinc oxide powder based on the total weight of the formulation, and at least one antibiotic, wherein said formulation contains 80-97 weight % of said dextrin dispersion, based on the total weight of the formulation, and said dextrin dispersion contains 45-75 weight % solids, wherein said dextrin dispersion has a pH of 8-9 and a viscosity of 12,000-25,000 cp, and wherein said formulation heals a wound within at least one of the gastrointestinal, respiratory and urinary systems of a patient, and the adhesive formulation protects against dehiscences of anastomosis of at least one of the gastrointestinal, respiratory and urinary systems.

17. A non-toxic biological adhesive formulation for affixing a prosthesis in a patient during a hernia operation, said formulation comprising dextrin as a dispersion, at least one adhesiveness modifier agent comprising from 8 weight % to about 19 weight % zinc oxide powder based on the total weight of the formulation, and at least one antibiotic, wherein said formulation contains 80-97 weight % of said dextrin dispersion, based on the total weight of the formulation, and said dextrin dispersion contains 45-75 weight % solids, wherein said dextrin dispersion has a pH of 8-9 and a viscosity of 12,000-25,000 cp, and wherein said formulation affixes a prosthesis in a patient during a hernia operation.

18. A non-toxic biological adhesive formulation for occluding a fistula within a patient, said formulation comprising dextrin as a dispersion, at least one adhesiveness modifier agent comprising from 8 weight % to about 19 weight % zinc oxide powder based on the total weight of the formulation, and at least one antibiotic, wherein said formulation contains 80-97 weight % of said dextrin dispersion, based on the total weight of the formulation, and said dextrin dispersion contains 45-75 weight % solids, wherein said dextrin dispersion has a pH of 8-9 and a viscosity of 12,000-25,000 cp, and wherein said formulation occludes a fistula within a patient.

19. A non-toxic biological adhesive formulation for protecting and sealing anastomosis and suture lines in internal body cavities, said formulation comprising dextrin as a dispersion, at least one adhesiveness modifier agent comprising from 8 weight % to about 19 weight % zinc oxide powder based on the total weight of the formulation, and at least one antibiotic, wherein said formulation contains 80-97 weight % of said dextrin dispersion, based on the total weight of the formulation, and said dextrin dispersion contains 45-75 weight % solids, wherein said dextrin dispersion has a pH of 8-9 and a viscosity of 12,000-25,000 cp, and wherein said formulation is biodegradable and metabolized products thereof are non-toxic.

20. A non-toxic biological, adhesive formulation for protecting and sealing anastomosis and suture lines in internal body cavities, said formulation comprising dextrin as a dispersion, at least one adhesiveness modifier agent comprising from 8 weight % to about 19 weight % zinc oxide powder based on the total weight of the formulation, and at least one antibiotic, wherein said formulation contains 80-97 weight % of said dextrin dispersion, based on the total weight of the formulation, and said dextrin dispersion contains 45-75 weight % solids, wherein said dextrin dispersion has a pH of 8-9 and a viscosity of 12,000-25,000 cp, and wherein said formulation is biodegradable and biocompatible.

21. A non-toxic biological adhesive formulation for temporarily protecting and sealing anastomosis and suture lines in internal body cavities, said formulation comprising dextrin as a dispersion, at least one adhesiveness modifier agent comprising from 8 weight % to about 19 weight % zinc oxide powder based on the total weight of the formulation, and at least one antibiotic, wherein said formulation contains 80-97 weight % of said dextrin dispersion, based on the total weight of the formulation, and said dextrin dispersion contains 45-75 weight % solids, wherein said dextrin dispersion as a pH of 8-9 and a viscosity of 12,000-25,000 cp, and wherein said formulation is biologically degradable and provides temporary protection and sealing of anastomosis and suture lines from the 2nd to the 14th post-operative day.

22. A non-toxic biological adhesive formulation for protecting and sealing anastomosis and suture lines in internal body cavities, said formulation comprising dextrin as a dispersion, at least one adhesiveness modifier agent comprising from 8 weight % to about 19 weight % zinc oxide powder based on the total weight of the formulation, and at least one antibiotic, wherein said formulation contains 80-97 weight % of said dextrin dispersion, based on the total weight of the formulation, and said dextrin dispersion contains 45-73 weight % dextrin solids, wherein said dextrin dispersion has a pH of 3-9 and a viscosity of 12,000-25,000 cp, and wherein said formulation protects and seals anastomosis and suture lines in internal body cavities.

23. A non-toxic biological adhesive formulation for protecting and sealing anastomosis and suture lines in internal body cavities, said formulation comprising dextrin as a dispersion, at least one adhesiveness modifier agent comprising from 8 weight % to about 19 weight % zinc oxide powder based on the total weight of the formulation, and at least one antibiotic, wherein said formulation contains 80-97 weight % of said dextrin dispersion, based on the total weight of the formulation, and said dextrin dispersion contains 45-75 weight % dextrin solids, wherein said dextrin dispersion has a pH of 8-9 and a viscosity of 12,000-25000 cp, and wherein said formulation protects and seals an anastomosis and provides temporary protection of the anastomosis from the $2^{nd}$ to the $14^{th}$ post-operative days.

24. An adhesive formulation according to claim 17, wherein said formulation contains 8-19 weight % of said at least one adhesiveness modifier agent, based on the total weight of the formulation.

* * * * *

UNITED STATES PATENT AND TRADEMARK OFFICE
CERTIFICATE OF CORRECTION

PATENT NO. : 8,252,333 B2
APPLICATION NO. : 11/507623
DATED : August 28, 2012
INVENTOR(S) : Jorge Cueto-Garcia It is certified that error appears in the above-identified patent and that said Letters Patent is hereby corrected as shown below:

In the Specification:

(1) On column 7, at line 29, "the surrounding organs and structures, for" should read
--the surrounding organs and structures. For--.

(2) On column 8, at line 49, "tomosis is particularly week because collagen" should read
--tomosis is particularly weak because collagen--.

(3) On column 13, at line 61, "L. P. Fielding el al described in the British Medical Journal" should
read --L.P. Fielding et al. described in the British Medical Journal--.

(4) On column 16, at line 30, "Then, a 3 cm 2 patch of cellulose or collagen" should read
--Then, a 3 $cm^2$ patch of cellulose or collagen--.

(5) On column 21, at line 29, "12:940=945" should read
--12:940-945--.

In the Claims:

(6) On column 24, at line 14, "a pH of 3-9 and a viscosity of 12,000-25,000 cp," should read
--a pH of 8-9 and a viscosity of 12,000-25,000 cp--.

Signed and Sealed this
Nineteenth Day of March, 2013

Teresa Stanek Rea
*Acting Director of the United States Patent and Trademark Office*